(12) United States Patent
Rochkind et al.

(10) Patent No.: US 8,242,076 B2
(45) Date of Patent: Aug. 14, 2012

(54) POLYPEPTIDES, MATRICES, HYDROGELS AND METHODS OF USING SAME FOR TISSUE REGENERATION AND REPAIR

(75) Inventors: Shimon Rochkind, Tel-Aviv (IL); Zvi Nevo, Herzlia (IL)

(73) Assignees: Ramot at Tel-Aviv University Ltd., Tel-Aviv (IL); The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 307 days.

(21) Appl. No.: 12/673,520

(22) PCT Filed: Aug. 13, 2008

(86) PCT No.: PCT/IL2008/001120
§ 371 (c)(1),
(2), (4) Date: Feb. 15, 2010

(87) PCT Pub. No.: WO2009/022339
PCT Pub. Date: Feb. 19, 2009

(65) Prior Publication Data
US 2011/0104225 A1 May 5, 2011

Related U.S. Application Data

(60) Provisional application No. 60/935,487, filed on Aug. 15, 2007.

(51) Int. Cl.
*A61K 38/00* (2006.01)
*A61K 9/14* (2006.01)
(52) U.S. Cl. ..................... 514/16.5; 514/18.8; 514/18.6; 424/484
(58) Field of Classification Search ................. 514/18.8, 514/18.6, 16.5; 424/484
See application file for complete search history.

(56) References Cited

U.S. PATENT DOCUMENTS 6,184,348 B1 2/2001 Ferrari et al.
2007/0065415 A1* 3/2007 Kleinsek et al. ............. 424/93.7

FOREIGN PATENT DOCUMENTS

WO WO 2007/030469 3/2007
WO WO 2009/022339 2/2009

OTHER PUBLICATIONS

Communication Pursuant to Article 94(3) EPC Dated Jan. 11, 2011 From the European Patent Office Re. Application No. 08789794.8.
International Preliminary Report on Patentability Dated Feb. 25, 2010 From the International Bureau of WIPO Re.: Application No. PCT/IL2008/001120.
International Search Report Dated Dec. 1, 2008 From the International Searching Authority Re.: Application No. PCT/IL2008/001120.
Written Opinion Dated Dec. 1, 2008 From the International Searching Authority Re.: Application No. PCT/IL2008/001120.
Bellamkonda et al. "Laminin Oligopeptide Derivatized Agarose Gels Allow Three-Dimensional Neurite Extension In Vitro", Journal of Neuroscience Research, XP002059315, 41(4): 501-509, Jul. 1, 1995.
Santiago et al. "Peptide-Surface Modification of Poly(Capolactrone) With Laminin-Derived Sequences for Adipose-Derived Stem Cell Applications", Biomaterials, XP005287267, 27(15): 2962-2969, May 1, 2006. Abstract.
Yu et al. "Guided Cell Adhesion and Ougrowth in Peptide-Modified Channels for Neural Tissue Engineering", Biomaterials, XP004621560, 26(13): 1507-1514, May 1, 2005.

* cited by examiner

*Primary Examiner* — Maryam Monshipouri (57) ABSTRACT

A novel laminin polypeptide comprising the amino acid sequence set forth by SEQ ID NO:3 is disclosed. Also disclosed are compositions-of-matter comprising a polysaccharide (e.g., hyaluronic acid) and the novel laminin polypeptide; or hyaluronic acid, a laminin polypeptide and an antioxidant (e.g., superoxide dismutase), as well as matrices and hydrogels comprising same which can be used for ex vivo or in vivo tissue formation and for treatment of pathologies characterized by diseased, damaged or loss of tissue.

24 Claims, 5 Drawing Sheets
(5 of 5 Drawing Sheet(s) Filed in Color)

Structure of the active site of 50D

KSIKVAVRSYIGSRCV

SEQ ID NO:1 — SIKVAV (SEQ ID NO:2)
SEQ ID NO:2 — YIGSR
Full sequence KSIKVAVRSYIGSRCV (SEQ ID NO:3)

POLYPEPTIDES, MATRICES, HYDROGELS AND METHODS OF USING SAME FOR TISSUE REGENERATION AND REPAIR

RELATED APPLICATIONS

This Application is a National Phase of PCT Patent Application No. PCT/IL2008/001120 having International filing date of Aug. 13, 2008, which claims the benefit of U.S. Provisional Patent Application No. 60/935,487 filed on Aug. 15, 2007. The contents of the above Applications are all incorporated herein by reference.

FIELD AND BACKGROUND OF THE INVENTION

The present invention, in some embodiments thereof, relates to compositions comprising a novel laminin polypeptide and, more particularly, but not exclusively, to matrices and hydrogels comprising same and methods of using same.

Hydrated gels (hydrogels) are viscous, semisolid entities at physiological temperatures and pH which can be used for tissue engineering, regenerative medicine and as biomaterials. For example, hydrogels were prepared from polysaccharides (Coviello et al, 2007) such as hyaluronic acid (e.g., using hybrid combinations of hyaluronic acid with calcium phosphate, chitosan, gelatin or alginate) or chitosan (e.g., chitosan with laminin peptides; Suzuki et. al., 2003; Itoh et. al., 2005; Matzuda et. al., 2005, Ho et. al., 2005) as well as from synthetic materials such as Poly(2-hydroxyethyl methacrylate). Hyaluronic acid-based hydrogels provide a growth supportive milieu for cells and tissues such as for nerve regeneration (Suzuki et. al., 2003; Itoh et. al., 2005), while guiding migration and regeneration of nutritional-trophic and anti oxidative agents.

Laminins are basement membrane glycoproteins which function as adhesive molecules, mediating and interacting with cytoskeleton's bound integrins, cadherins, cell adhesive molecules (CAMs) and extracellular matrix (ECM) constituents and support cell migration, attachment, proliferation, differentiation and survival. Hyaluronic acid-based hydrogels which were modified with laminin were shown to promote neurite extension (Hou et. al., 2005). Certain laminin sequence repeats were found to have a biological activity on cell surface receptors. These include IKVAV (SEQ ID NO:1) and YIGSR (SEQ ID NO:2) which serve as guiding tracks for migration, regeneration and growth (Tashiro et. al., 1989; Powell and Kleinmann, 1997; Niece et. al., 2003; Hallmann et. al., 2005).

The primary defense mechanism against oxidative stress is the enzyme superoxide dismutase (SOD) which catalyzes the dismutation of superoxide anion free radical ($O_2^-$) to hydrogen peroxide ($H_2O_2$) and oxygen ($O_2$). Hydrogels which include SOD from bovine erythrocytes conjugated to sodium hyaluronate were found to be non-immunogenic in mice and exhibited much higher anti-inflammatory activities than HA or SOD alone (Sekurai et. al., 1997). In addition, SOD was found to inhibit not only reactive oxygen species (ROS) induction but also HA depolymerization which is caused by mechanical stress (Yamazaki et. al., 2003).

Additional background art includes Hartman J R., 1986 (Proc. Natl. Acad. Sci. 83: 7142-7146).

SUMMARY OF THE INVENTION

According to an aspect of some embodiments of the present invention there is provided a polypeptide comprising the amino acid sequence set forth by SEQ ID NO:3.

According to an aspect of some embodiments of the present invention there is provided a composition-of-matter comprising a polysaccharide and the polypeptide of the invention.

According to an aspect of some embodiments of the present invention there is provided a composition-of-matter comprising hyaluronic acid, a laminin polypeptide and an antioxidant.

According to an aspect of some embodiments of the present invention there is provided a composition-of-matter comprising hyaluronic acid, superoxide dismutase (SOD) and the polypeptide of the invention.

According to an aspect of some embodiments of the present invention there is provided a matrix comprising the composition-of-matter of the invention.

According to an aspect of some embodiments of the present invention there is provided a hydrogel comprising the composition-of-matter of the invention.

According to an aspect of some embodiments of the present invention there is provided a method of generating a hydrogel, the method comprising suspending the composition-of-matter of the invention in water so as to obtain a suspension which comprises at least 80% water, thereby generating the hydrogel.

According to an aspect of some embodiments of the present invention there is provided a method of inducing ex vivo formation of a tissue, comprising: (a) providing the matrix or the hydrogel of the invention, and; (ii) seeding the matrix or the hydrogel with cells in a medium suitable for proliferation, differentiation and/or migration of the cells, thereby inducing the formation of the tissue.

According to an aspect of some embodiments of the present invention there is provided a method of inducing in vivo formation of a tissue, the method comprising implanting the matrix or the hydrogel of the invention in a subject, thereby inducing the formation of the tissue.

According to an aspect of some embodiments of the present invention there is provided a method of treating a subject having a pathology characterized by diseased, damaged or loss of tissue, the method comprising implanting the matrix or the hydrogel of the invention at or near the diseased, damaged or loss tissue of the subject, thereby inducing the formation of the tissue and treating the subject.

According to some embodiments of the invention, the polysaccharide is hyaluronic acid.

According to some embodiments of the invention, the composition-of-matter further comprising an antioxidant.

According to some embodiments of the invention, the antioxidant is superoxide dismutase (SOD).

According to some embodiments of the invention, the laminin polypeptide is set forth by SEQ ID NO:3.

According to some embodiments of the invention, the laminin polypeptide consisting of the amino acid sequence set forth by SEQ ID NO:3.

According to some embodiments of the invention, the superoxide dismutase comprises the amino acid sequence set forth by SEQ ID NO:4.

According to some embodiments of the invention, the composition-of-matter being cross linked.

According to some embodiments of the invention, the polysaccharide, the antioxidant and/or the polypeptide are cross linked.

According to some embodiments of the invention, the hyaluronic acid, the superoxide dismutase (SOD) and the polypeptide are cross linked.

According to some embodiments of the invention, the method further comprising cross linking the composition-of-matter.

According to some embodiments of the invention, cross-linking is effected using a cross linking agent selected from the group consisting of EDC-N-(3-dimenthy-aminoprophyl)-N-ethyl carbodiimide, DVS-divinyl sulfone and genipin.

According to some embodiments of the invention, the suspension comprises at least 95% water.

According to some embodiments of the invention, the hyaluronic acid is provided at a concentration range of about 0.5-1.5% in the hydrogel.

According to some embodiments of the invention, the polypeptide is provided at a concentration range of about 20-100 µg/ml in the hydrogel.

According to some embodiments of the invention, the superoxide dismutase is provided at a concentration range of about 5-40 µg/ml in the hydrogel.

According to some embodiments of the invention, the matrix or the hydrogel further comprising cells.

According to some embodiments of the invention, the tissue is a neural tissue.

According to some embodiments of the invention, the cells are stem cells.

According to some embodiments of the invention, the stem cells differentiate into neuronal cells when seeded in the matrix or the hydrogel.

According to some embodiments of the invention, the hydrogel being lyophilized.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

The patent or application file contains at least one drawing executed in color. Copies of this patent or patent application publication with color drawing(s) will be provided by the Office upon request and payment of the necessary fee.

In the drawings:

FIG. 2A—primary cells cultured in the presence of the Eagle's culture medium stained with Bodian's silver stain. Note the monolayers of cells and the absence of aggregates of differentiated cells (Magnification, ×100); FIG. 2B—Primary cells covered with 1.2% hyaluronic acid hydrogel and stained Bodian's silver stain. Note the cell aggregates (Magnification ×200); FIG. 2C—Primary cells covered with the hyaluronic acid-superoxide dismutase-laminin peptide (SEQ ID NO:3) hydrogel and stained Bodian's silver stain. Note the differentiated neuronal cells, with typical neuronal growth, cell associations into aggregates and conglomerates with intensive axonal sprouting (Magnification ×200). FIGS. 2D-F—Primary cells grown covered with the hyaluronic acid-superoxide dismutase-laminin peptide (SEQ ID NO:3) hydrogel and stained crystal violet stain. Note differentiated neuronal cells with intensive axonal sprouting. Magnifications are ×200 in FIGS. 2D and E and ×400 in FIG. 2F.

DESCRIPTION OF SPECIFIC EMBODIMENTS OF THE INVENTION

The present invention, in some embodiments thereof, relates to compositions comprising a novel laminin polypeptide and, more particularly, but not exclusively, to matrices and hydrogels comprising same and methods of using same for tissue formation, regeneration and/or repair.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have designed a novel laminin polypeptide (SEQ ID NO:3) which is capable of supporting proliferation, differentiation and/or migration of cells, such as neuronal cells. The novel laminin polypeptide includes the two laminin pentapeptides IKVAV (SEQ ID NO:1) and YIGSR (SEQ ID NO:2) and three dimers designed as potential sites of cross-linking: a dimer (KS) in the N-terminal position, a second dimer (RS) inbetween the two penta peptides and a third dimmer (CV) at the carboxy terminal.

Thus, as shown in the Examples section which follows, the present inventors have generated a polysaccharide (hyaluronic acid)—based hydrogel which comprises the novel laminin polypeptide and an antioxidant (superoxide dismutase). When mixed with stem cells, the hydrogel was capable of inducing neuronal cell differentiation (Example 2, and FIGS. 2C-F). In contrast, hyaluronic acid-based hydrogels devoid of the novel laminin polypeptide failed to support neuronal cell differentiation (Example 2, FIG. 2B). In addition, cross-linking of the hydrogel components using Genipin did not reduce hydrogel's abilities to support cell's proliferation and differentiation (Example 2).

Thus, according to one aspect of the invention, there is provided an isolated polypeptide which comprises the amino acid sequence set forth by SEQ ID NO:3.

The terms "polypeptide" or "peptide" which are interchangeably used herein, encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

Table 1.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |

TABLE 2-continued

| Non-conventional amino acid | Code | Non-conventional amino acid | Code |
|---|---|---|---|
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |

TABLE 2-continued

| Non-conventional amino acid | Code | Non-conventional amino acid | Code |
|---|---|---|---|
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine N-(N-(2,2-diphenylethyl) carbamylmethyl-glycine | Mval Nnbhm  Nnbhm | L-N-methylhomophenylalanine N-(N-(3,3-diphenylpropyl) carbamylmethyl(1)glycine | Nmhphe  Nnbhe |
| 1-carboxy-1-(2,2-diphenyl ethylamino)cyclopropane | Nmbc | | |

Table 2.

The peptides of the present invention are preferably utilized in a linear form, although it will be appreciated that in cases where cyclicization does not severely interfere with peptide characteristics, cyclic forms of the peptide can also be utilized.

Since the present peptides can be utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55(3):227-50.

In cases where large amounts or long polypeptides (e.g., longer than 20 amino acids) are desired, the polypeptides of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Polypeptides of the present invention can be combined with a polysaccharide so as to generate a hydrogel or a matrix.

The polysaccharide can be extracted and isolated from an organism such as a bacterium (e.g., Pseudomonas sp NCIB 11264, U.S. Pat. No. 4,298,725) or can be synthetically produced by chemically reacting carbohydrate subunits (e.g., sugars such as glucose, glucosamine, N—Ac-glcNH$_2$, uronic acid or other monosaccharides or disaccharides) under suitable conditions (see for example, U.S. Pat. No. 5,558,899). The polysaccharide may have a linear or branched structure and a molecular weight from about 10,000 Daltons to about 3×10$^6$ Daltons.

According to some embodiments of the invention, the polysaccharide is biologically inert having a low rate of reactivity with other substances under ordinary conditions.

According to some embodiments of the invention, the polysaccharide is biocompatible, e.g., when in contact with cells, tissues or body fluid of an organism does not induce adverse effects such as immunological reactions and/or rejections, cellular death, and the like. A biocompatible polysaccharide can also be biodegradable.

According to some embodiments of the invention, the polysaccharide is capable of forming highly hydrated gels in aqueous solutions.

Examples of suitable polysaccharides include, but are not limited to, hyaluronic acid [e.g., sodium hyaluronate (Na-HA), Hou S, et al., 2005, J. Neurosci. Methods. June 21; Epub ahead of print], alginate, agarose, chitosan, pectin, synthetic polymers such as methylcellulose, polyglycolic acid and polylactic acid (e.g., Fukuhara S., et al. Circ. J. 69:850-7, 2005), hyaluronic acid (HA) hydrogels, cellulose, glycogen, starch, maltodextrin, dextran, β-glucan, laminarin and chitin. According to some embodiments of the invention, the polysaccharide of the invention is hyaluronic acid.

According to some embodiments of the invention, the composition-of-matter further comprises an antioxidant which can protect cells or macromolecules (e.g., the polysaccharide) from oxidative stress (oxidative damage caused by free radicals). Thus, the antioxidant can extend the survival of the macromolecules by preventing their oxidative depolymerization.

Non-limiting examples of suitable antioxidants include molecules such as glutathione, vitamin C (sodium ascorbate), vitamin E (tocopherols and tocotrienols), N-Ac-L-cysteine, hydroquinone, glutamate, or enzymes such as catalase, superoxide dismutase, glutathione peroxidase or other peroxidases, and glucose-6-phosphate dehydrogenase (G6PD) (see Osmen I., Naziroglu M., Okutan R. Comparative study of antioxidant enzymes in tissues surrounding implant in rabbits. Cell. Biochem. Funct. 24:275-281, 2006).

Superoxide dismutase, in addition to its known activity as an antioxidant, can also serve as an anti-inflammatory agent when used in vivo. Non-limiting examples of superoxide dismutase (SOD) enzymes which can be used in the composition of the invention include, SOD-1 (soluble), SOD-2 (mitochondrial) or SOD-3 (extracellular), such as *homo sapiens* soluble superoxide dismutase 1 (SOD-1) GenBank Accession No. NP_000445 (SEQ ID NO:4); *homo sapiens* mitochondrial superoxide dismutase 2 (SOD-2) GenBank Accession Nos. NP_001019637.1 (isoform B), NP_001019636.1 (isoform A), NP_000627.2 (isoform A); *homo sapiens* extracellular superoxide dismutase 3 (SOD-3) GenBank Accession No. NP_003093.2; *Saccharomyces cerevisiae* SOD-1 GenBank Accession No. NP_012638.1; and Rattus norvegicus SOD-1 GenBank Accession No. NP_058746.

The antioxidant of the invention can be produced by recombinant techniques. For example, a polynucleotide encoding superoxide dismutase 1 (GenBank Accession No. NM_000454; SEQ ID NO:5) can be ligated into a nucleic acid construct suitable for expression in a host cell (e.g., bacterial cell, yeast cell, mammalian cell). Such a nucleic acid construct includes a promoter sequence for directing transcription of the polynucleotide sequence in the cell in a constitutive or inducible manner, and may also include sequences which render this vector suitable for replication and integration in prokaryotes, eukaryotes, or preferably both (e.g., shuttle vectors); transcription and translation initiation sequence, enhancers, transcription and translation terminator, and a polyadenylation signal which may increase the efficiency of mRNA translation; a signal sequence for secretion; sequences engineered to enhance stability, production, purification, yield or toxicity of the expressed polypeptide.

The antioxidant can be recovered and purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

According to some embodiments of the invention, the antioxidant is retrieved in "substantially pure" form. As used herein, the phrase "substantially pure" refers to a purity that allows for the effective use of the recombinant polypeptide as an antioxidant.

While further reducing the present invention to practice, the present inventors have uncovered that a composition-of-matter which comprises hyaluronic acid, a laminin polypeptide and superoxide dismutase (e.g., in a form of a hydrogel) can support neuronal cell differentiation.

The term "laminin" as used herein refers to the family of extracellular matrix glycoproteins, which form the major noncollagenous constituent of basement membrane. Laminins have been implicated in a wide variety of biological processes including cell adhesion, differentiation, migration, signaling, neurite outgrowth and metastasis. Laminins are composed of 3 non identical chains: laminin alpha, beta and gamma, each encoded by a distinct gene.

As used herein the phrase "laminin polypeptide" refers to an amino acid sequence which comprises at least 4 consecutive amino acids of a laminin polypeptide and which exhibits a biological activity (e.g., support cell growth, proliferation, differentiation and/or migration).

According to some embodiments of the invention the laminin polypeptide can include an amino acid sequence of a laminin alpha-chain such as LAMA1 (e.g., GenBank Accession No. NP_005550.2), LAMA2 (e.g., GenBank Accession Nos. NP_000417.2 and NP_001073291.1), LAMA3 (e.g., GenBank Accession Nos. NP_937762.1 and NP_000218.2), LAMA4 (e.g., GenBank Accession Nos. NP_001098677.1, NP_001098676.1, NP_002281.2, NP_001098679.1, and NP_001098678.1), and LAMA5 (e.g., GenBank Accession No. NP_005551.3); a laminin beta-chain such as LAMB1 (e.g., GenBank Accession No. NP_002282.1), LAMB2 (e.g., GenBank Accession No. NP_002283.3), LAMB3 (e.g., GenBank Accession Nos. NP_000219.2 and NP_001017402.1) and LAMB4 (e.g., GenBank Accession No. NP_031382.2); and/or a laminin gamma-chain such as LAMC1 (e.g., GenBank Accession No. NP_002284.3), LAMC2 (e.g., GenBank Accession Nos. NP_005553.2 and NP_061486.2) and LAMC3 (e.g., GenBank Accession No. NP_006050.3).

According to some embodiments of the invention the laminin polypeptide includes a repeated amino acid sequence (e.g., a 4 or 5 amino acid repeated sequence) of a laminin sequence.

Non-limiting examples of laminin polypeptides which can be included in the composition-of-matter of the invention include the peptides set forth in SEQ ID NO:1, 2 or 3.

It should be noted that since the components comprised in the composition-of-matter of the invention can be prepared using synthetic or recombinant techniques they are obtainable as highly pure, sterile preparations of analytical or pharmaceutical grade.

As mentioned above, the present inventors have generated a hydrogel from a polysaccharide (hyaluronic acid), an antioxidant (superoxide dismutase) and the novel laminin polypeptide set forth by SEQ ID NO:3 (see Example 1 of the Examples section which follows).

Thus, according to an aspect of some embodiments of the invention, there is provided a method of generating a hydrogel. The method comprising suspending the composition-of-matter of the invention in water so as to obtain a suspension which comprises at least about 50% water, thereby generating the hydrogel.

As used herein, the term "hydrogel" refers to a material comprising the composition-of-matter of the invention and water, in which the water constitutes more than 50%.

According to some embodiments of the invention, the hydrogel comprises at least about 60% water, at least about 70% water, at least about 80% water, at least about 90% water, at least about 95% water, at least about 96% water, at least about 97% water, at least about 98% water, at least about 99% water.

According to some embodiments of the invention, the hyaluronic acid is provided at a concentration range of about 0.3-2%, e.g., about 0.4-1.8%, e.g., about 0.5-1.6, e.g., about 0.5-1.5%, e.g., about 0.6-1.4%, e.g., about 0.8-1.2%, e.g., about 1.2% in the hydrogel.

According to some embodiments of the invention, the laminin polypeptide (e.g., SEQ ID NO:3) is provided at a concentration range of about 10-200 µg/ml, e.g., about 20-100 µg/ml, e.g., about 50 µg/ml in the hydrogel.

According to some embodiments of the invention, superoxide dismutase is provided at a concentration range of about 8 μM (about 0.25 microgram/ml) to 8 mM (about 250 microgram/ml) in the hydrogel. For example, superoxide dismutase can be provided at a concentration range of about 0.5 μg/ml to about 200 μg/ml, e.g., from about 1 μg/ml to about 100 μg/ml, e.g., from about 2 μg/ml to about 80 μg/ml, e.g., from about 4 μg/ml to about 40 μg/ml, e.g., from about 5 μg/ml to about 50 μg/ml, e.g., from about 10 μg/ml to about 50 μg/ml, e.g., from about 15 μg/ml to about 40 μg/ml, e.g., from about 20 μg/ml to about 30 μg/ml, e.g., about 25 μg/ml.

According to some embodiments of the invention, the method further comprising cross-linking the composition-of-matter.

Cross-linking (i.e., binding via covalent or ionic bonds) of the components comprised in the composition-of-matter (e.g., the polysaccharide, the antioxidant and the laminin polypeptide) can be performed using any cross-linking or coupling agent known in the art.

Non-limiting examples of suitable cross-linking agents include dimethyl suberimidate (an imidoester crosslinker); Bis(Sulfosuccinimidyl) suberate (BS3; an NHS-ester crosslinker); formaldehyde; 1-Ethyl-3-]3-dimethylamino-propyl]carbodiimide hydrochloride (EDC; the carbodiimide crosslinker); N-hydroxyuccinimide (NHS) [Mao J. S, et al., Biomaterials. 24,1621-1629, 2003; Choi Y. S., et al., J. Biomed. Mater. Res. 48,631-639, 1999; Richert L., et al., Biomacromolecules, 5, 284-294, 2004)]; Divinyl sulfone (DVS); and genipin [Sung H. W., et al., J Biomed. Mater. Res. A, 64A:427-438, 2003; Chen S C., et al., J. Control Release. 96, 285-300, 2004; Mwale F., et al., Tissue Eng., 11, 130-40, 2005; Chen H., et al., Biomacromolecules, 7, 2091-2098, 2006].

For ex vivo or in vivo cross-linking photo-reactive amino acid analogs (e.g., diazirine analogs to leucine and methionine) can be added to the composition-of-matter and following exposure to ultraviolet light, the diazirines are activated and bind to interacting side chains (e.g., carboxyl or amino groups).

According to some embodiments of the invention, cross-linking is performed using a non-toxic and/or biocompatible agent. Examples include, but are not limited to 3-dimenthy-aminoprophyl)-N-ethyl carbodiimide (EDC-N; Sigma-Aldrich-Fluka, St Louis, Mo. 63178, Catalogue No. 03459), divinyl sulfone (DVS; Sigma, Catalogue No. V-370-0) and genipin (Sigma Catalogue No. G-4796).

According to some embodiments of the invention, the hydrogel is lyophilized by methods well known in the art such that a dry matrix is obtained. It should be noted that water-free matrices can be preserved for long periods of time without being subjected to enzymatic degradation or contamination (e.g., by microorganisms).

As used herein the phrase "matrix" refers to a two-dimensional or a three-dimensional supporting framework comprising the composition of the invention.

The matrix can be kept in a dry or wet form, or can be frozen according to the intended use.

It should be noted that the dry matrix can be further hydrated in an aqueous solution (e.g., water) until a hydrogel is formed.

According to some embodiments of the invention, the hydrogel or the matrix further comprise cells (see Example 2 which follows) such as stem cells or differentiated cells.

As used herein the phrase "stem cell" refers to cells which are capable of remaining in an undifferentiated state (e.g., pluripotent or multipotent stem cells) for extended periods of time in culture until induced to differentiate into other cell types having a particular, specialized function (e.g., fully differentiated cells).

Non-limiting examples of stem cells which can be used by the invention include embryonic stem cells, induced pluripotent stem cells (iPS), hematopoietic stem cells (e.g., bone marrow stem cells, cord blood cells, peripheral blood stem cells), adult stem cells and mesenchymal stem cells.

Non-limiting examples of differentiated cells which can be used by the invention include neural cells, retina cells, epidermal cells, hepatocytes, pancreatic cells, osseous cells, cartilaginous cells, elastic cells, fibrous cells, myocytes, myocardial cells, endothelial cells, smooth muscle cells, and hematopoietic cells (e.g., lymphocytes).

According to some embodiments of the invention, the stem cells are neuronal progenitor cells (such as those obtained from embryonic or fetal neuronal tissue or brain).

As mentioned above and described in Example 2 (e.g., FIGS. 2C-F) when seeded with stem cells derived from fetal brain, the hydrogel enabled the differentiation of the cells to neuronal cells.

Thus, according to an aspect of some embodiments of the invention, there is provided a method of inducing ex vivo formation of a tissue. The method is effected by (a) providing the matrix or the hydrogel of the invention and (ii) seeding the matrix or the hydrogel with cells in a medium suitable for proliferation, differentiation and/or migration of the cells, thereby inducing the formation of the tissue.

The phrase "tissue" refers to a group of cells that perform a similar function. Examples include, but are not limited to, brain tissue, neuronal tissue, retina, skin tissue, hepatic tissue, pancreatic tissue, bone, cartilage, connective tissue, blood tissue, muscle tissue, cardiac tissue, vascular tissue, renal tissue, pulmonary tissue, gonadal tissue, hematopoietic tissue. According to some embodiments of the invention, the phrase "tissue" also encompasses an "organ", i.e., a fully differentiated structural and functional unit in an animal that is specialized for some particular function. Non-limiting examples of organs include head, brain, eye, bone (e.g., of leg and hand), heart, liver kidney, lung, pancreas, ovary, testis, and stomach.

According to some embodiments of the invention the tissue is a neural tissue.

The term "seeding" refers to plating, placing and/or dropping the cells of the within, under or on the matrix or the hydrogel of the invention.

The concentration of the seeded cells depends on the type of cells used and the concentration of the matrix or hydrogel's components.

The medium used according to this aspect of the invention can be any tissue culture medium suitable for inducing the proliferation, differentiation and/or migration of the cells (e.g., stem cells) of the invention into more specialized (i.e., differentiated) cells. According to some embodiments of the invention the culture medium is supplemented with minerals, amino acids and/or nutrients (e.g., Eagle's culture medium supplemented with glutamine and glucose as described in Example 2 which follows), or further with serum and/or growth factors.

Following seeding, the matrices or the hydrogels are routinely examined using a microscope (e.g., an inverted microscope, an axioplan light microscope or an electronic microscope) for evaluation of cell growth, spreading and tissue formation (see for example FIGS. 2A-F).

According to some embodiments of the invention, the ex vivo formed tissue can be further implanted in a subject. In such cases the cells seeded within the matrix or the hydrogel can be derived from the treated individual (autologous source) or from allogeneic sources such as embryonic stem cells which are not expected to induce an immunogenic reaction.

As used herein, the term "subject" includes both young and old human beings of both sexes. According to some embodiments of the invention, the term encompasses individuals who suffer from a pathology as described below.

According to an aspect of the invention there is provided a method of inducing tissue formation in vivo, and/or treating a subject having a pathology characterized by diseased, damaged or loss of tissue. The method is effected by implanting the matrix or the hydrogel of the invention in the subject, such as at or near the diseased, damaged or loss tissue of the subject, thereby inducing the formation of the tissue and/or treating the subject.

As used herein the phrase "pathology characterized by diseased, damaged or loss of tissue" refers to any disorder, disease or condition exhibiting a tissue damage (i.e., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration. Examples of disorders or conditions requiring tissue regeneration include, but are not limited to, liver cirrhosis such as in hepatitis C patients (liver), Type-1 diabetes (pancreas), cystic fibrosis (lung, liver, pancreas), bone cancer (bone), burn and wound repair (skin), age related macular degeneration (retina), myocardial infarction, myocardial repair, CNS lesions (myelin), articular cartilage defects (chondrocytes), bladder degeneration, intestinal degeneration, and the like.

The phrase "treating" refers to inhibiting or arresting the development of a disease, disorder or condition and/or causing the reduction, remission, or regression of a disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

Those of skills in the art are capable of determining when and how to implant the matrix or the hydrogel to thereby induce tissue formation within the subject. See for example, Artzi Z, et al., 2005, J. Clin. Periodontol. 32: 193-9; Butler C E and Prieto V G, 2004, Plast. Reconstr. Surg. 114: 464-73.

The compositions, the matrix and/or the hydrogel of the invention may, if desired, be presented in a pack or dispenser device, such as an FDA approved kit, or an article-of-manufacturing (with packaging material), which may contain one or more unit dosage forms containing the active ingredient. The pack may, for example, comprise metal or plastic foil, such as a blister pack. The pack or dispenser device may be accompanied by instructions for administration, implantation and/or for ex vivo or in vivo forming, regenerating and/or repairing a tissue and/or treating a subject. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. The compositions, matrix or hydrogel of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of means "including and limited to".

The term "consisting essentially of means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Hyaluronic Acid-Superoxide Dismutase and a Laminin Peptide Hydrogels Hyaluronic acid—Sodium hyaluronate is a naturally occurring high molecular weight ($3\times10^6$ daltons) linear polysaccharide which is found in the extracellular matrix of connective tissues, skin, cartilage, synovial fluids, in the vitreous humour of the eye and in many other places. Sodium hyaluronate (Na-HA) is pharmacologically inert polymer, forming in aqueous solutions highly hydrated gel formats with viscoelastic features. Such preparations are utilized: (1) as an opthalmological surgical aid, maintaining eye tissue organelles intact during surgery e.g. intraocular lens insertion, intra and extra capsular lens extraction, cataract and glaucoma surgery, corneal graft surgery, retinal detachment and vitreal replacement procedure; (2) in joint replacement procedures Na-HA injections serves as visco-supplementation ameliorating the inflammatory status and inflammatory mediators, serving as an anti inflammatory agents and anti-inflammatory mediators, serving for neutralizing free radicals and oxidative agents by its own (HA) cleavage and depolymerising; and (iii) new avenues were open employing HA as a friendly biomaterial, integrated in tissue engineered constructs, scaffolds gels as cells' and tissues' supportive structures, guiding, migration and regeneration, used as cavities filler upon tumor resection. In turn HA is easily eliminated-cleaved by the enzyme hyaluronidase, creating empty routes for cell migration.

Figure 1:
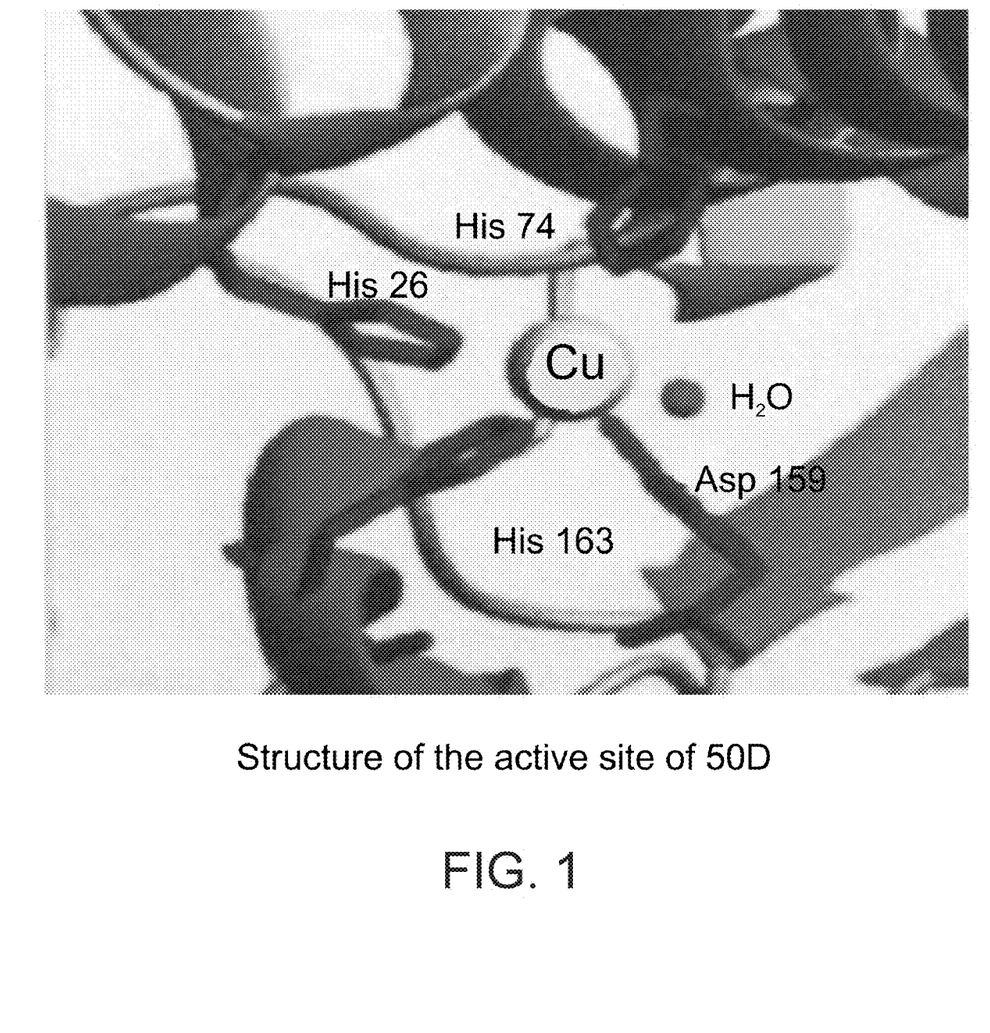
FIG. 1 is a prior art schematic illustration depicting the redox active site of a superoxide dismutase (SOD) homologue which includes three histidine residues (His 26, 74 and 163) and an aspartic acid residue (Asp 159) surrounding the catalytic active metal cation (copper, Cu in this case). Alternative metal cations are zinc (Zn), manganese (Mn) and ferrous (Fe).

Superoxide dismutase—The human cytosolic Cu—Zn—SOD found in the cytoplasm of cells is a homodimer of a molecular weight of 32,500 daltons. The two identical subunits are joined primarily by hydropholic and electrostatic interactions. The ligands of copper and zinc are the histidine side chains (FIG. 1)

Figure 3:
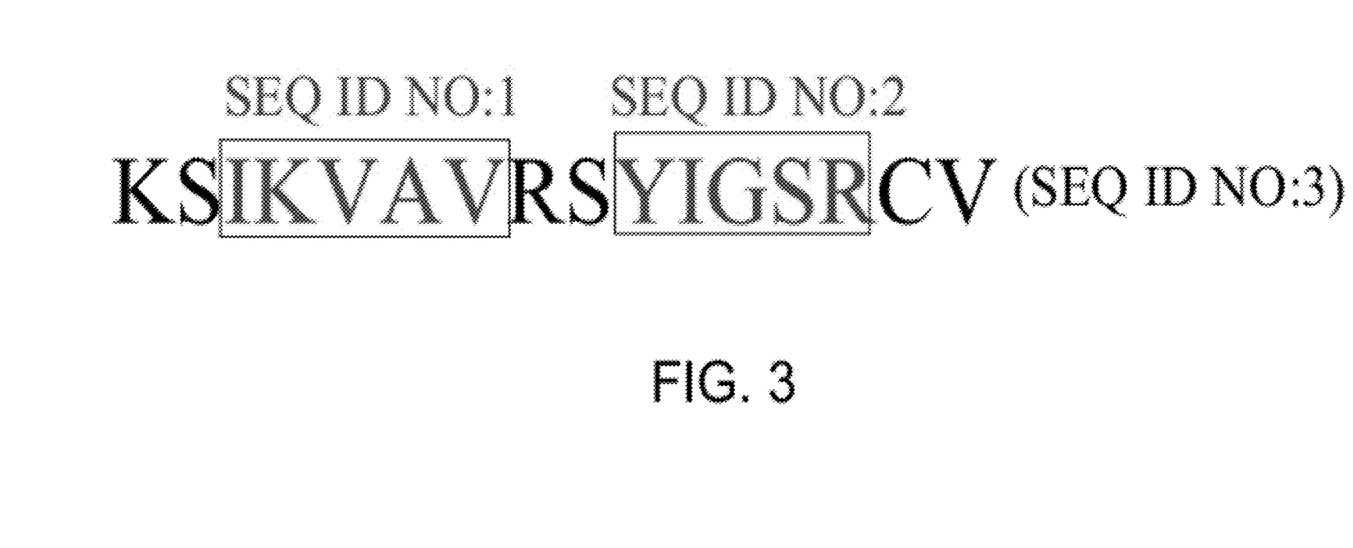
FIG. 3 is a schematic illustration depicting the sequence of the novel laminin peptide of the invention (SEQ ID NO:3) which is composed of the two pentapeptides (boxed sequences) comprising the amino acid sequences set forth by SEQ ID NOs:1 and 2 (shown in red) and 3 additional dimers: a dimer in the N-terminal position (KS), a second dimer inbetween the two penta peptides (RS), and a third at the tail-carboxy terminal (CV).

Generation of a novel laminin synthetic peptide: KSIKVAVRSYIGSRCV (SEQ ID NO:3)—The laminin peptide (SEQ ID NO:3) contains two penta peptides: the IKVAV (SEQ ID NO:1) and YIGSR (SEQ ID NO:2) sequences, mimicking the activities of an intact laminin molecules on neurons, and 3 additional dimers: a dimer in the N-terminal position (KS), a second dimer inbetween the two penta peptides (RS), and a third at the tail-carboxy terminal (CV) (See FIG. 3). The dimers were placed as spacers and as potential sites for cross linking which should therefore not interrupt the sequence of the two penta peptides (SEQ ID NOs:1 and 2).

Cross linking agents—Cross-linking agents form covalent bonds between the three elements (Na-HA; LN peptide; Cu—Zn-SOD) composing the hydrogel. In order to form covalent bonds without loosing the biological activities of the bonded elements during cross linking, several cross linking agents can be used, such as EDC-N-(3-dimenthy-aminoprophyl)-N-ethyl carbodiimide, DVS-divinyl sulfone and genipin. Basically the principles of cross linking is combining free primary amino groups with carboxyl groups, or oxidizing in between close hydroxyl groups, forming reactive aldehydes, to interact either among themselves or with amines of additional conjugate may be formed via tiol residues.

Materials and Experimental Methods

Sodium Hyaluronate—Sodium hyaluronate (HA) was produced by Bio-Technology General (BTG) Corporation Ltd. (Kiryat Weizmann, Rehovot 76326 and Be'er Tuvia, Industrial Zone, P.O. Box 571, Kiryat Malachi, 83104 Israel) from the *Streptococcus* strain selected on the basis of its high amounts of capsule secretion. It is obtained as a highly purified agent, from the secreted capsules undergoing multi steps purification resulting in a sterile preparation free of protein, nitrogen or pyrogen substances.

Cu, Zn Super Oxide Dismutase (Cu—Zn-SOD)—SOD [EC 1.15.1.1, soluble *homo sapiens* superoxide dismutase 1; GenBank Accession No. NP_000445 (SEQ ID NO:4 for polypeptide) and GenBank Accession No. NM 000454 (SEQ ID NO:5 for polynucleotide)] was recombinantly produced in bacteria (*E. coli*) by BTG Ltd (Savient et. Ferring) essentially as described in Hartman J R., et al., 1986 (Proc. Natl. Acad. Sci. USA, Vol: 83, pp 7142-7146).

Synthesis of the novel laminin peptide (SEQ ID NO:3)—was performed by Elim Biopharmacenticals, Inc. Hayward, Calif. 94545, USA.

Generation of hydrogel—For the preparation of a 10 ml hydrogel, 120 mg of sodium hyaluronate (HA) was solubilized in water for 24 hours using a magnetic stirrer, following which 50 µl of SOD (5 mg/ml) and 500 µg of the laminin peptide (SEQ ID NO:3, as a dry powder) were added and mixed in the hydrogel.

Analytical Determinations of the Elements Composing the Hydrogel:

Na-hyaluronate—Total content of HA is determined based on the content of uronic acids (lucuronic acid) by the routine test of Dische (Dische Z. A new specific color reaction of hexuronic Acids. J. Biol. Chem, 167, 189-197, 1947) employing the carbazol reagent. The molecular weight of HA is evaluated by viscosity measurement with a digital viscosimeter Brookfield brand Cone/Plate DVII+Per (Brookfield Engineering Laboratories Inc. Middleboro, Mass. 02346-1031 USA). The molecular weight of HA can be calculated as well by the discrepancy between the figure obtained in Dische's assays versus the data obtained by Park-Johnson (Park J. T. Johnson M. J. A submicrodetermination of glucose J. Biol. Chem. 181, 149-151, 1949)) determination for reducing sugars.

Determination of Superoxide Dismutase Activity—SOD activity was measured at 560 nm as the rate of suppression of reduction of nitrotetrazolium blue when superoxide anion radical was generated during oxidation of xanthine by xanthine oxidase. The reaction mixture contained 50 mM sodium carbonate dissolved in 50 mM K, Na-phosphate buffer (pH 7.8 at 25 °C.), 0.1 mM EDTA, 0.1 mM xanthine, 0.025 mM nitrotetrazolium blue. For 1 unit of activity, the amount of protein was taken which provided 50% inhibition of nitrotetrazolium blue reduction under standard conditions. Membrane-bound Mn-containing SOD can be determined as the difference between total SOD activity and that of Cu/Zn-enzyme determined after treatment of the sample with 2% SDS Cu/Zn-SOD was measured in cytosolic fraction of tissues and in lysates obtained from cells.

LN's active peptides determination—The penta peptides of LN are detected by specific antibodies to IKVAV (SEQ ID NO:1) and YIGSR (SEQ ID NO:2), or an anti-laminin antibody (Sigma Cat. No. #L 9393, Sigma-Aldrich, Israel) using immunohistochemical staining procedures.

Experimental Results

The present inventors generated a hydrogel from the following three elements: sodium hyaluronate, a novel laminin peptide (SEQ ID NO:3) and an antioxidant (e.g., SOD).

Such a hydrogel exhibit unique physical features: (i) The hydrogel coexists with films coating plastic surfaces e.g. fibronectin, polylysine; (ii) the hydrogel's conductivity in isotonic salt solution (medium) is 11.0 mOhm/cm (for comparison, the conductivity of HA alone is 1.37 mOhm/cm); (iii) the hydrogel is viscous, for example, 1% HA, at 100 rpm and 25° C., 82 centipoise; (iv) the hydrogel is transparent; and (v) the hydrogel is a slow releaser of content of added ingredients.

The hyaluronic acid-hyaluronate component (NaHA) in the hydrogel is (i) a linear, stretched, high molecular weight, highly hydrated hyaluronic acid (HA) sodium salt. Concentrations range between 0.5% to 1.5%; (ii) a polyanionic polymer formed with only a carboxylic group at each dimmer. Other potential low reactive groups, hydroxyl groups and N-acetylated amines; (iii) creating a hydrogel construct with a viscosity pending in the HA concentration; (iv) a friendly milieu preserving the gaseous atmospheric environment, and protecting the trophic added agents, at room temperature, outside the incubator; and (v) characterizing the healthy environment in fetal life, supporting a fast and perfect scar less wound healing.

The unique hydrogel features can be preserved for long terms as a hydrogel solution, with slow released ingredients for weeks to 1-2 months or without ingredients, added prior to use for longer periods; biocompatible (no inflammation mediators are evoked); biodegradable, within the regenerative-healing period of the reparative tissue.

This hydrogel can be used to support growth, proliferation and differentiation of various cells such as neuronal cells. The hydrogel can affect density of sprouting axons proliferation in neuronal rich cultures, as well as in composite neuronal rich implants transplanted in vivo, significantly more than in cultures and implants not including such a hydrogel. Thus, when applied on injured peripheral nerve with massive losses, an accelerated pace of regeneration, healing and function, is expected.

The unique hydrogel developed by the present inventors simulate the extracellular milieu, and can support cells in vitro and in vivo upon implantation and be used as a space cavity filler, e.g. lumens created upon removal of neoplasmas.

The formulation of the hydrogel from the three elements HA, SOD and LN peptides (Na-HA 1.2%; LN peptide 50 µg/ml, SOD 25 µg/ml) covalently cross linked has many defined virtues: Extended molecular intactness of HA macromolecules due to the SOD protection from oxidative damages of depolymerization. Both SOD molecules and high molecular weight HA chains serve as anti-inflammatory agents, ameliorating the inflammatory mediators status. SOD diminishes the oxidative stress conditions created in cultures and in implanted transplantations construct in vivo. The laminin synthetic peptide designed herein (SEQ ID NO:3) presents most of the positive virtues of the biological activities of laminin without the disadvantages of immunogenic reactions evoked by the whole laminin macromolecules. Furthermore, a major source for laminin (LN-1) is its isolation from mice with Engelbreth-Holm-Swarm ascite tumor, has a disadvantage for clinical use. The cross linked construct retaining the full scale biological activities of its constituents, exerts a tremendous virtues, where all the functional groups reside closely topographically together. Overcoming the critical time periods of hostile harsh conditions in and around the implants by the antioxidant activity of SOD and the guarding features of the LN peptides ensures the survival of the implant, to be renourished by the diffusible nutrient starting to arrive from the surroundings.

Example 2

Ex Vivo Differentiation of Neuronal Progenitor Cells Into Neurons Within the Hyaluronuc Acid-Superoxide Dismutase and Laminin Peptide Hydrogels Material and Experimental Methods Cells—Dissociated, undifferentiated stem cells derived from rat cerebral hemispheres at 16-18 days of gestation were prepared as previously described (Reshef et. al., 1996; Reshef, A., Sperling, O., Zoref-Shan E. Preconditioning of primary rat neuronal cultures against ischemic injury: characterization of the time window of protection. Brain Res. 741, 252-257, 1996). The cells were maintained on plastic dishes with Eagle's culture medium [Eagle's basal medium containing Earle's salts (Sigma, St. Louis, Mo.) supplemented with 2 mM glutamine and 5 mg/ml glucose (Biological Industries, Kibbuts Beit Haemek, Israel)] in a 95% air and 5% $CO_2$, in a humidified atmosphere, at 37° C. For testing the various culture conditions, the cells were cultured on the plastic dishes in the presence of the Eagle's for 3 days without changing the medium, following which the medium was changed and the cells were further cultured for additional 12 days on the plastic dishes in the presence of the medium (control, culture conditions "i") or were covered with various hydrogels (culture conditions "ii", "iii" and "iv") as follows:

Culture Conditions (i) Control cultures included cells cultured in the presence of Eagle's culture medium and maintained on plastic dishes;

(ii) Hyaluronic acid hydrogel cultures—1.2% hyaluronic acid was added to the attached cells at the third day post seeding;

(iii) Hyaluronic acid—laminin peptide—antioxidant hydrogel cultures—on the third day in culture the cells were cultured in the presence of mixed hyaluronic acid (1.2%), a synthetic peptide of laminin (50 µg/ml) made of 16 amino acids (SEQ ID NO:3; KSIKVAVRSYIGSRCV) and an antioxidant (Cu—Zn superoxide dismutase (Cu—Zn-SOD, 25 μg/ml).

(iv) Cross-linked hyaluronic acid—laminin peptide—antioxidant hydrogel cultures—on the third day in culture the cells were cultured in the presence of cross-linked hyaluronic acid (1.2%), a synthetic peptide of laminin (50 μg/ml) made of 16 amino acids (SEQ ID NO:3; KSIKVAVRSYIGSRCV) and an antioxidant (Cu—Zn superoxide dismutase (Cu—Zn-SOD, 25 μg/ml). The cross linker agent used in most experiments was Genipin, although other cross linking agents such as Carbodiimide, divinyl sulfone or just sugars (monosaccharides) have been successfully employed as a cross linker.

Nissl staining procedure for neurons—Crystal violet 0.1% (0.1 gram in 100 ml distilled water plus 10 drops of glacial acetic acid, filtering just before use). The stain detects Nissl bodies in the cytoplasm of neurons in cultures or tissue sections fixed in formalin and embedded in paraffin. The Nissl bodies are stained purple-blue to pink-violet. Additional neuron's specific staining procedures: Bodian's silver method described in Pearse (1972; Pearse, A. Histochemistry, Theoretical and Applied. Vols 1 & 2, 3rd edition, Little, Brown & Co, Boston, Mass., 1972); immunohistochemical procedures: anti MAP-2; anti GAP-43, or anti neurospecific enolase are used further to assess the differentiating neurons.

Experimental Results

Figure 2A:
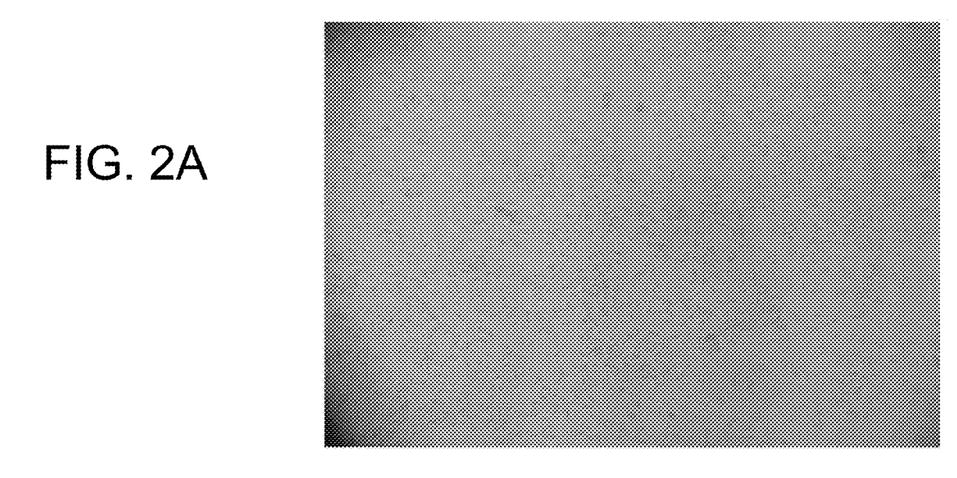
FIGS. 2A-F are microscopic photographs of primary cells stained with Bodian's silver stain (FIGS. 2A-C) or crystal violet stain (FIGS. 2D-F) under various culturing conditions. Primary fetal rat brain cells derived from cerebral hemispheres of rat embryos (16 to 18 day of gestation) were cultured for 3 days on plastic dishes in the presence of the Eagle's culture medium (Eagle's basal medium supplemented with 2 mM glutamine and 5 mg/ml glucose) following which the cells were either covered with a hydrogel [1.2% hyaluronic acid hydrogel (FIG. 2B) or hyaluronic acid-superoxide dismutase-laminin peptide (SEQ ID NO:3) hydrogel (FIGS. 2C-F)] or with the Eagle's culture medium and were further cultured for additional 12 days, stained and photographed.
Figure 2B:
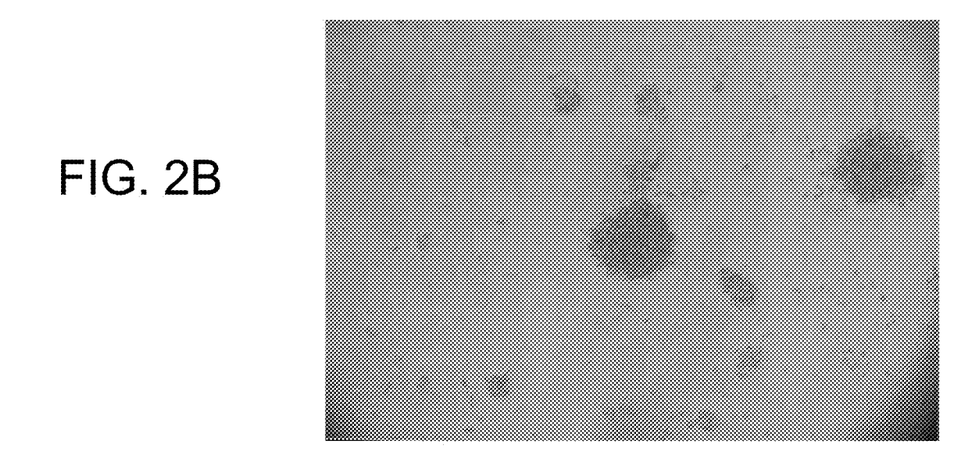
Figure 2C:
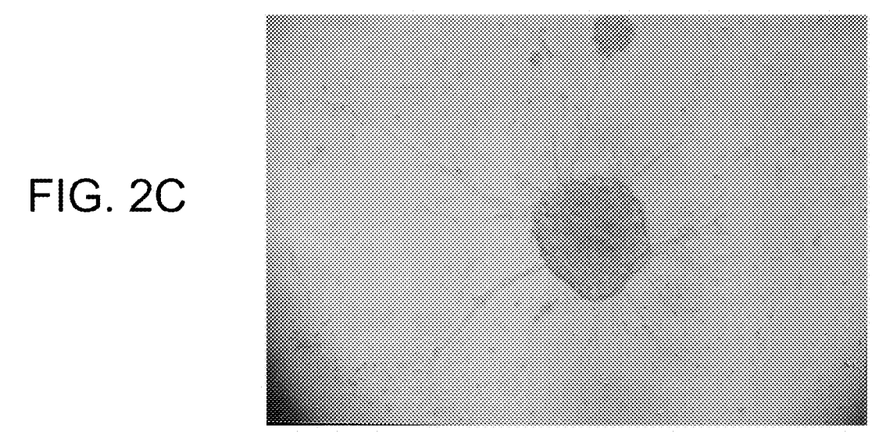
Figure 2D:
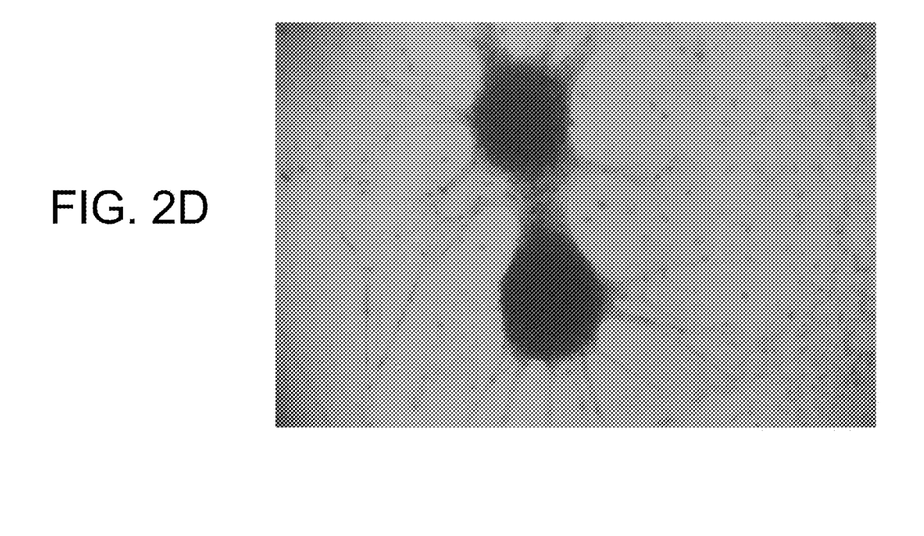
Figure 2E:
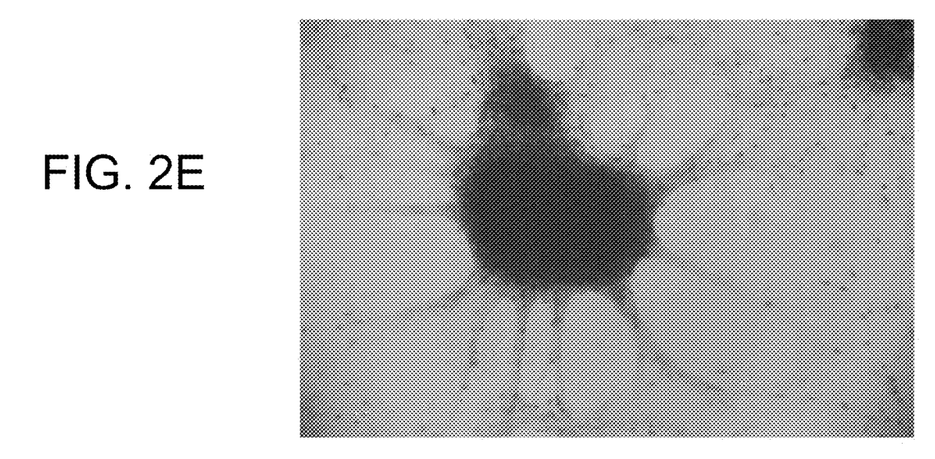
Figure 2F:
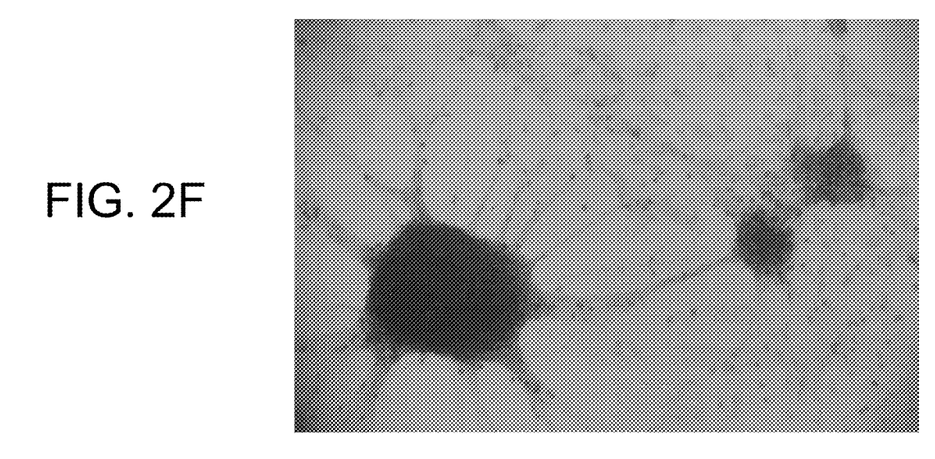

As shown in FIG. 2A, control cultures maintained on plastic dishes, exhibited the growth of a non-confluent monolayered cultures. In contrast, in cultures growing in the presence of 1.2% hyaluronic acid hydrogel the cells tend to form cell aggregates (conglomerates) (FIG. 2B). The third type of cultures included cells growing in the presence of a hydrogel containing hyaluronic acid (1.2%), the synthetic laminin peptide (SEQ ID NO:3; 50 μg/ml) and the Cu—Zn superoxide dismutase (Cu—Zn-SOD, 25 μg/ml) antioxidant. As shown in FIGS. 2C-F, cells grown with a hydrogel containing hyaluronic acid, laminin peptide (SEQ ID NO:3) and the Cu—Zn superoxide dismutase formed cell aggregates accompanied with intensive dendrite sprouting, simulating mature functional neurons.

It should be noted that primary cells cultured in hydrogels which included mixed constituents (culture iii) or cross-linked constituents (culture iv) were not significantly different from each other (data not shown). Thus, to prevent possible dissertation of the small molecular weight constituents (e.g. the laminin peptide and/or SOD) out of the hydrogel, the hydrogels can be cross-linked without loosing their intrinsic characteristics and ability to support proliferation, differentiation and migration of cells.

Hydrogels which included hyaluronic acid, SOD and the laminin synthetic peptide (SEQ ID NO:3) which serves as a guiding growth factor, drive the cells cultured therein towards differentiation, e.g., neurogenesis, while superoxide dismutase serves as a neuroprotectant agent.

Further treatment of the aggregates by, e.g., subculturing the cells after trypsinization, is expected to release and spread out migrating neurons. Such cultures growing in the presence of the hydrogel containing hyaluronic acid, laminin peptide (SEQ ID NO:3) and the Cu—Zn superoxide dismutase can be utilized as 3D constructs for further transplantation, regeneration into injured, degenerated or missing neuronal elements in vivo, readily adjusted with dense fibers for implantation into damaged peripheral nerves tissue.

As a collaborative work with Prof Eyal Zusmann from the Technion, Israel, a polycaprolactone (PCL) tube of 2 mm in diameter was used as a bridge for a massive region loss, connecting the two stumps of the torn peripheral nerve. The tubes were filled with a hydrogel containing hyaluronic acid (1.2%), the synthetic laminin peptide (SEQ ID NO:3; 50 μg/ml) and Cu—Zn superoxide dismutase (Cu—Zn-SOD, 25 microgram/ml), versus control of naked tubes. A higher density of neuronal sprouting was observed in one out of two injured rats, demonstrating a complete and perfect bridging of 2 cm region loss. These studies demonstrate the use of the hydrogel of some embodiments of the invention for neuronal tissue regeneration and repair.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

Coviello T., Matricardi P., Marianecci C., Alhaique F. Polysaccharide hydrogels for modified release formulations. J Controlled Release. 119, 5-24, 2007.

Hallmann R., Horn N., Selg M., Wendler O., Pausch F., Sorokin L. M. Expression and function of laminins in the embryonic and mature vasculature. Physiol. Rev. 85, 979-1000, 2005.

Hartman J R., 1986., Proc. Natl. Acad. Sci. 83: 7142-7146.

Ho M. H., Wang D. M., Hsieh H. J., Liu H. C., Hsien T. Y., Lai J. Y., Hou L. T. Preparation and characterization of RGD-immobilized chitosan scaffolds. Biomaterials. 26, 3197-3206, 2005.

Hou S., Xu Q., Tian W., Cui F., Cai Q., Ma J., Lee I. S. The repair of brain by implantation of hyaluronic acid hydrogels modified with laminin. J. Neurosci. Met. 148, 60-70, 2005.

Itoh S., Matsuda A., Kobayashi H., Ichinose S., Shinomiya K., Tanaka J. Effects of a laminin peptide (YIGSR) immobilized on crab-tendon chitosan tubes on nerve regeneration. J Biomed. Mater. Res. B Appl. Biomater. 73, 375-382, 2005.

Matsuda A., Kobayashi H., Itoh S., Kataoka K., Tanaka J. Immobilization of laminin peptide in molecularly aligned chitosan by covalent bonding. Biomaterials 26, 2273-2279, 2005.

Niece K. L, Hartgerink J. D, Donners J. J, Stupp S. I. Self-assembly combining two bioactive peptide-amphiphile molecules into nanofibers by electrostatic attraction. J. Am. Chem. Soc. 125, 7146-7147, 2003

Powell S. K., Kleinman H. K. Neuronal laminins and their cellular receptors. Int. J. Biochem. Cell Biol. 29, 401-414, 1997.

Sekurai K., Miyazaki K., Kodera Y., Nishimura H., Shingu M., Inada Y. Anti-inflammatory activity of superoxide dismutase conjugated with sodium hyaluronate. Glycoconjugate J. 14:723-728, 1997.

Suzuki M., Itoh S., Yamaguchi I., Takakuda K., Kobayashi H., Shinomiya K., Tanaka J. Tendon chitosan tubes covalently coupled with synthesized laminin peptides facilitate nerve regeneration in vivo. J Neurosci. Res.72, 646-659, 2003.

Tashiro K., Sephel G. C., Weeks B., Sasaki M., Martin G. R., Kleinman H. K.,

Yamada Y. A synthetic peptide containing the IKVAV sequence from the A chain of laminin mediates cell attachment, migration, and neurite outgrowth. J Biol Chem. 264, 16174-16182, 1989.

Yamazaki K., Fukuda K., Matsukawa M., Hara F., Matsushita T., Yamamoto N., Yoshida K., Munakata H., Hamanishi C. Cyclic tensile stretch loaded on bovine chondrocytes causes depolymerization of hyaluronan: involvement of reactive oxygen species. Arthritis & Rheum, 48:3151-3158, 2003.

What is claimed is:

1. A polypeptide comprising the amino acid sequence set forth by SEQ ID NO:3.

2. A composition-of-matter comprising a polysaccharide and the polypeptide of claim 1.

3. The composition-of-matter of claim 2, wherein said polysaccharide is hyaluronic acid.

4. The composition-of-matter of claim 2, further comprising an antioxidant.

5. A composition-of-matter comprising hyaluronic acid, a laminin polypeptide, set forth in SEQ ID NO:3, and an antioxidant.

6. A composition-of-matter comprising hyaluronic acid, superoxide dismutase (SOD) and the polypeptide of claim 1.

7. The composition-of-matter of claim 6, wherein said superoxide dismutase comprises the amino acid sequence set forth by SEQ ID NO:4.

8. The composition-of-matter of claim 4, wherein said polysaccharide, said antioxidant and/or said polypeptide are cross linked.

9. The composition-of-matter of claim 6, wherein said hyaluronic acid, said superoxide dismutase (SOD) and said polypeptide are cross linked.

10. A matrix comprising the composition-of-matter claim 2.

11. A hydrogel comprising the composition-of-matter of claim 2.

12. A method of generating a hydrogel, the method comprising suspending the composition-of-matter of claim 2 in water so as to obtain a suspension which comprises at least 80% water, thereby generating the hydrogel.

13. The method of claim 12, further comprising cross linking the composition-of-matter.

14. The hydrogel of claim 11, wherein said polypeptide is provided at a concentration range of about 20-100 µg/ml in said hydrogel.

15. A method of inducing ex vivo formation of a tissue, comprising:

(a) providing the hydrogel of claim 13 and;

(ii) seeding said hydrogel with cells in a medium suitable for proliferation, differentiation and/or migration of said cells, thereby inducing the formation of the tissue.

16. A method of inducing in vivo formation of a tissue, the method comprising implanting the hydrogel of claim 11 in a subject, thereby inducing the formation of the tissue.

17. A method of treating a subject having a pathology characterized by diseased, damaged or loss of tissue, the method comprising implanting the hydrogel of claim 11 at or near the diseased, damaged or loss tissue of the subject, thereby inducing the formation of the tissue and treating the subject.

18. The method of claim 15, wherein said tissue is a neural tissue.

19. The method of claim 15, wherein said cells are stem cells.

20. A method of inducing ex vivo formation of a tissue, comprising:

(a) providing the matrix of claim 10, and;

(ii) seeding said matrix with cells in a medium suitable for proliferation, differentiation and/or migration of said cells, thereby inducing the formation of the tissue.

21. A method of inducing in vivo formation of a tissue, the method comprising implanting the matrix of claim 10 in a subject, thereby inducing the formation of the tissue.

22. A method of treating a subject having a pathology characterized by diseased, damaged or loss of tissue, the method comprising implanting the matrix of claim 10 at or near the diseased, damaged or loss tissue of the subject, thereby inducing the formation of the tissue and treating the subject.

23. A method of inducing skin regeneration in a subject in need thereof, the method comprising implanting the matrix of claim 10 in the subject, thereby inducing skin regeneration.

24. A method of inducing skin regeneration in a subject in need thereof, the method comprising implanting the hydrogel of claim 11 in the subject, thereby inducing skin regeneration.

\* \* \* \* \*

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial sequence
<220> FEATURE:
<223> OTHER INFORMATION: Laminin mimicking synthetic peptide

<400> SEQUENCE: 1

Ile Lys Val Ala Val
1               5

<210> SEQ ID NO 2
<211> LENGTH: 5
<212> TYPE: PRT
<213> ORGANISM: Artificial sequence
<220> FEATURE:
<223> OTHER INFORMATION: Laminin mimicking synthetic peptide

<400> SEQUENCE: 2

Tyr Ile Gly Ser Arg
1               5

<210> SEQ ID NO 3
<211> LENGTH: 16
<212> TYPE: PRT
<213> ORGANISM: Artificial sequence
<220> FEATURE:
<223> OTHER INFORMATION: Laminin mimicking synthetic peptide

<400> SEQUENCE: 3

Lys Ser Ile Lys Val Ala Val Arg Ser Tyr Ile Gly Ser Arg Cys Val
1               5                  10                  15

<210> SEQ ID NO 4
<211> LENGTH: 154
<212> TYPE: PRT
<213> ORGANISM: Homo sapiens

<400> SEQUENCE: 4

Met Ala Thr Lys Ala Val Cys Val Leu Lys Gly Asp Gly Pro Val Gln
1               5                  10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95
```

```
Asp Val Ser Ile Glu Asp Ser Val Ile Ser Leu Ser Gly Asp His Cys
            100                 105                 110
Ile Ile Gly Arg Thr Leu Val Val His Glu Lys Ala Asp Asp Leu Gly
                115                 120                 125
Lys Gly Gly Asn Glu Glu Ser Thr Lys Thr Gly Asn Ala Gly Ser Arg
    130                 135                 140
Leu Ala Cys Gly Val Ile Gly Ile Ala Gln
145                 150

<210> SEQ ID NO 5
<211> LENGTH: 981
<212> TYPE: DNA
<213> ORGANISM: Homo sapiens

<400> SEQUENCE: 5
gtttggggcc agagtgggcg aggcgcggag gtctggccta taaagtagtc gcggagacgg     60
ggtgctggtt tgcgtcgtag tctcctgcag cgtctggggt ttccgttgca gtcctcggaa    120
ccaggacctc ggcgtggcct agcgagttat ggcgacgaag gccgtgtgcg tgctgaaggg    180
cgacggccca gtgcagggca tcatcaattt cgagcagaag gaaagtaatg gaccagtgaa    240
ggtgtgggga agcattaaag gactgactga aggcctgcat ggattccatg ttcatgagtt    300
tggagataat acagcaggct gtaccagtgc aggtcctcac tttaatcctc tatccagaaa    360
acacggtggg ccaaaggatg aagagaggca tgttggagac ttgggcaatg tgactgctga    420
caaagatggt gtggccgatg tgtctattga agattctgtg atctcactct caggagacca    480
ttgcatcatt ggccgcacac tggtggtcca tgaaaaagca gatgacttgg gcaaaggtgg    540
aaatgaagaa agtacaaaga caggaaacgc tggaagtcgt ttggcttgtg gtgtaattgg    600
gatcgcccaa taaacattcc cttggatgta gtctgaggcc ccttaactca tctgttatcc    660
tgctagctgt agaaatgtat cctgataaac attaaacact gtaatcttaa aagtgtaatt    720
gtgtgacttt ttcagagttg ctttaaagta cctgtagtga gaaactgatt tatgatcact    780
tggaagattt gtatagtttt ataaaactca gttaaaatgt ctgtttcaat gacctgtatt    840
ttgccagact taaatcacag atgggtatta aacttgtcag aatttctttg tcattcaagc    900
ctgtgaataa aaaccctgta tggcacttat tatgaggcta ttaaaagaat ccaaattcaa    960
actaaaaaaa aaaaaaaaa a                                               981
```